(12) United States Patent
Kerwin et al.

(10) Patent No.: US 7,700,722 B2
(45) Date of Patent: Apr. 20, 2010

(54) COMPOSITIONS OF PEGYLATED SOLUBLE TUMOR NECROSIS FACTOR RECEPTORS AND METHODS OF PREPARING

(75) Inventors: Bruce Kerwin, Thousand Oaks, CA (US); Byeong Chang, Thousand Oaks, CA (US); Lei Shi, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1057 days.

(21) Appl. No.: 10/461,839

(22) Filed: Jun. 12, 2003

(65) Prior Publication Data
US 2003/0236196 A1 Dec. 25, 2003

Related U.S. Application Data

(63) Continuation-in-part of application No. 10/177,566, filed on Jun. 20, 2002, now abandoned.

(51) Int. Cl.
A61K 38/19 (2006.01)
(52) U.S. Cl. .......................... 530/350; 530/402; 514/2; 514/561
(58) Field of Classification Search ................ 435/188, 435/69.1; 514/2; 530/351
See application file for complete search history.

(56) References Cited

U.S. PATENT DOCUMENTS

| | | | |
|---|---|---|---|
| 4,002,531 A | 1/1977 | Royer | 195/68 |
| 4,421,920 A | 12/1983 | Baudouin | 546/163 |
| 4,597,966 A | 7/1986 | Zolton et al. | |
| 5,237,054 A | 8/1993 | Brinks et al. | |
| 5,714,350 A | 2/1998 | Co et al. | |
| 5,824,784 A | 10/1998 | Kinstler | 530/399 |
| 5,834,594 A | 11/1998 | Hakimi | 530/351 |
| 5,908,826 A | 6/1999 | Fukuda et al. | |
| 5,955,448 A | 9/1999 | Colaco et al. | |
| 6,171,586 B1 | 1/2001 | Lam et al. | |
| 6,177,077 B1 | 1/2001 | Tobinick | |
| 6,267,958 B1 | 7/2001 | Andya et al. | |
| 6,485,932 B1 | 11/2002 | McIntosh et al. | |
| 6,875,432 B2 | 4/2005 | Liu et al. | |
| 6,989,147 B2 | 1/2006 | Fisher | |
| 6,994,847 B2 | 2/2006 | Wolfe et al. | |
| 7,592,004 B2 | 9/2009 | Kaisheva et al. | |
| 2003/0054439 A1* | 3/2003 | Fisher et al. | 435/69.1 |
| 2003/0113316 A1 | 6/2003 | Kaisheva et al. | |
| 2003/0124119 A1 | 7/2003 | Yamazaki et al. | |
| 2003/0138417 A1 | 7/2003 | Kaisheva et al. | |
| 2004/0009168 A1 | 1/2004 | Kaisheva et al. | |
| 2004/0018200 A1 | 1/2004 | Oliver et al. | |
| 2004/0038878 A1 | 2/2004 | Tanikawa et al. | |
| 2004/0170623 A1 | 9/2004 | Arvinte et al. | |
| 2007/0243185 A1 | 10/2007 | Gombotz et al. | |

FOREIGN PATENT DOCUMENTS

| | | |
|---|---|---|
| EP | 0 025 275 | 3/1981 |
| EP | 0 025 321 | 3/1981 |
| EP | 0 025 719 | 3/1981 |
| EP | 0 308 378 B1 | 11/1994 |
| WO | WO 92/16221 | 10/1992 |
| WO | WO 95/34326 | 12/1995 |
| WO | WO 96/19459 | 6/1996 |
| WO | WO 97/12244 | 4/1997 |
| WO | WO 98/01555 | 1/1998 |
| WO | WO 2004/00211 | 12/2003 |

OTHER PUBLICATIONS

Edwards, C.K., et al. 1999 Ann Rheum Dis 58: (Suppl I) 173-181.*
Viscosity Reference Chart.*
Volume Guidelines for Compound Administration.*
Engelmann et al., "Antibodies to a Soluble Form of a Tumor Necrosis Factor (TNF) Receptor Have TNF-like Activity" *Journal of Biological Chemistry*, vol. 265 (24), pp. 14497-14504, 1990.
Cimzia® (certolizumab pegol) product insert, UCB, Inc., 1950 Lake Park Drive, Smyrna, GA 30080, US License No. 1736, Apr. 18, 2008.
Enbrel® (etanercept) product insert, Immunex Corporation, Seattle, WA 98101, US License No. 1132, 1999.
Enbrel® (etanercept) US PI PFS product insert, Immunex Corporation, Thousand Oaks, CA 91320-1799, US License No. 1132, Mar. 8, 2006.
Humira™ (adalimumab) product insert, Abbott Laboratories, North Chicago, IL 60064, US License No. 0043, Dec. 2002.
Kerwin et al., "Interactions between PEG and type I soluble tumor necrosis factor receptor: Modulation by pH and by PEGylation at the N terminus," *Protein Science* 11:1825-1833, 2002.
Kinstler et al., "Characterization and Stability of N-terminally PEGylated rhG-CSF," *Pharmaceutical Research* 13(7): 996-1002, 1996.
Remicade (infliximab) product insert, ©Centocor, Inc. 2002, Malvern, PA 19355, US License No. 1242, Feb. 2002.
Simponi (golimumab) product insert, Centocor Ortho Biotech Inc., Horsham, PA 19044, US License No. 1821, Apr. 2009.
Solorzano et al., "Pharmacokinetics, immunogenicity, and efficacy of dimeric TNFR binding proteins in healthy and bacteremic baboon," *J Applied Physiology* 84: 1119-1130, 1998.
Wang et al., "Polyethylene Glycolated Recombinant TNF Receptor I Improves Insulitis and Reduces Incidence of Spontaneous and Cyclophosphamide-Accelerated Diabetes in Nonobese Diabetic Mice," *Endocrinology* 143(9): 3490-3497, 2002.
International Search Report, dated Oct. 27, 2005.
Notice of Allowance, U.S. Appl. No. 11/784,538, filed Apr. 6, 2007, Gombotz et al.
Zingerman et al., (1987), International Journal of Pharmaceutics, 36(2/3): 141-145.

* cited by examiner

*Primary Examiner*—Karen Cochrane Carlson
*Assistant Examiner*—Marsha M Tsay
(74) *Attorney, Agent, or Firm*—Randolph N. Mohr; Rosemary Sweeney; Paul B. Tran

(57) ABSTRACT

The present invention provides for improved compositions comprising a PEGsTNF-R1 which, in addition to having useful higher concentrations, demonstrate decreased viscosity (<400 cP) and improved stability.

16 Claims, No Drawings

SEQUENCE LISTING

```
<160> NUMBER OF SEQ ID NOS: 1

<210> SEQ ID NO 1
<211> LENGTH: 106
<212> TYPE: PRT
<213> ORGANISM: Homo sapiens

<400> SEQUENCE: 1

Met Asp Ser Val Cys Pro Gln Gly Lys Tyr Ile His Pro Gln Asn Asn
1               5                   10                  15

Ser Ile Cys Cys Thr Lys Cys His Lys Gly Thr Tyr Leu Tyr Asn Asp
            20                  25                  30

Cys Pro Gly Pro Gly Gln Asp Thr Asp Cys Arg Glu Cys Glu Ser Gly
        35                  40                  45

Ser Phe Thr Ala Ser Glu Asn His Leu Arg His Cys Leu Ser Cys Ser
    50                  55                  60

Lys Cys Arg Lys Glu Met Gly Gln Val Glu Ile Ser Ser Cys Thr Val
65                  70                  75                  80

Asp Arg Asp Thr Val Cys Gly Cys Arg Lys Asn Gln Tyr Arg His Tyr
                85                  90                  95

Trp Ser Phe Asn Leu Phe Gln Cys Phe Asn
            100                 105
```

US 7,700,722 B2

COMPOSITIONS OF PEGYLATED SOLUBLE TUMOR NECROSIS FACTOR RECEPTORS AND METHODS OF PREPARING

This application is a Continuation in Part of U.S. application Ser. No. 10/177,566, filed Jun. 20, 2002 now abandoned, which is hereby incorporated by reference.

BACKGROUND OF THE INVENTION

Inflammation is the body's defense reaction to injuries such as those caused by mechanical damage, infection or antigenic stimulation. An inflammatory reaction may be expressed pathologically when inflammation is induced by an inappropriate stimulus such as an autoantigen, is expressed in an exaggerated manner, or persists well after the removal of the injurious agents. Such inflammatory reaction may include the production of certain cytokines.

While the etiology of inflammation is poorly understood, considerable information has recently been gained regarding the molecular aspects of inflammation. This research has led to identification of certain cytokines which are believed to figure prominently in the mediation of inflammation. Cytokines are extracellular proteins that modify the behavior of cells, particularly those cells that are in the immediate area of cytokine synthesis and release. Tumor necrosis factors (TNFs) are a class of cytokines produced by numerous cell types, including monocytes and macrophages.

At least two TNFs have been previously described, specifically TNF alpha (TNF-α) and TNF beta (TNF-β or lymphotoxin), and each is active as a trimeric molecule and is believed to initiate cellular signaling by crosslinking receptors; Engelmann et al., *J. Biol. Chem.*, 265:14497-14504 (1990).

Several lines of evidence implicate TNF-α and TNF-β as major inflammatory cytokines. These known TNFs have important physiological effects on a number of different target cells which are involved in inflammatory responses to a variety of stimuli such as infection and injury. The proteins cause both fibroblasts and synovial cells to secrete latent collagenase and prostaglandin $E_2$ and cause osteocyte cells to stimulate bone resorption. These proteins increase the surface adhesive properties of endothelial cells for neutrophils. They also cause endothelial cells to secrete coagulant activity and reduce their ability to lyse clots. In addition they redirect the activity of adipocytes away from the storage of lipids by inhibiting expression of the enzyme lipoprotein lipase. TNFs also cause hepatocytes to synthesize a class of proteins known as "acute phase reactants," which act on the hypothalamus as pyrogens; Selby et al., *Lancet*, 1(8583):483 (1988); Starnes, Jr. et al., *J. Clin. Invest.*, 82:1321 (1988); Oliff et al., *Cell*, 50:555 (1987); and Waage et al., *Lancet*, 1(8529):355 (1987). Additionally, preclinical results with various predictive animal models of inflammation, including rheumatoid arthritis, have suggested that inhibition of TNF can have a major impact on disease progression and severity; Dayer et al., *European Cytokine Network*, 5(6):563-571 (1994) and Feldmann et al., *Annals Of The New York Academy Of Sciences*, 66:272-278 (1995). Moreover, recent preliminary human clinical trials in rheumatoid arthritis with inhibitors of TNF have shown promising results; Rankin et al., *British Journal Of Rheumatology*, 3(4):4334-4342 (1995); Elliott et al., *Lancet*, 344:1105-1110 (1995); Tak et al., *Arthritis and Rheumatism*, 39:1077-1081 (1996); and Paleolog et al., *Arthritis and Rheumatism*, 39:1082-1091 (1996).

Protein inhibitors of TNF are disclosed in the art. EP 308378 reports that a protein derived from the urine of fever patients has a TNF inhibiting activity. The effect of this protein is presumably due to a competitive mechanism at the level of the receptors. EP 308378 discloses a protein sufficiently pure to be characterized by its N-terminus. The reference, however, does not teach any DNA sequence or a recombinantly-produced TNF inhibitor.

Recombinantly-produced TNF inhibitors have also been taught in the art. For example, EP 393438 and EP 422339 teach the amino acid and nucleic acid sequences of a mature, recombinant human "30 kDa TNF inhibitor" (also known as a p55 receptor and as sTNFR-I) and a mature, recombinant human "40 kDa inhibitor" (also known as a p75 receptor and as sTNFR-II) as well as modified forms thereof, e.g., fragments, functional derivatives and variants. EP 393438 and EP 422339 also disclose methods for isolating the genes responsible for coding the inhibitors, cloning the gene in suitable vectors and cell types, and expressing the gene to produce the inhibitors. Mature recombinant human 30 kDa TNF inhibitor and mature recombinant human 40 kDa TNF inhibitor have been demonstrated to be capable of inhibiting TNF (EP 393438, EP 422339, PCT WO 92/16221 and PCT WO 95/34326).

sTNFR-I and sTNFR-II are members of the nerve growth factor/TNF receptor superfamily of receptors which includes the nerve growth factor receptor (NGF), the B cell antigen CD40, 4-1BB, the rat T-cell antigen MRC OX40, the Fas antigen, and the CD27 and CD30 antigens; Smith et al., *Science*, 248:1019-1023 (1990). The most conserved feature amongst this group of cell surface receptors is the cysteine-rich extracellular ligand binding domain, which can be divided into four repeating motifs of about forty amino acids and which contains 4-6 cysteine residues at positions which are well conserved; Smith et al., supra.

EP 393438 further teaches a 40 kDa TNF inhibitor •51 and a 40 kDa TNF inhibitor •53, which are truncated versions of the full-length recombinant 40 kDa TNF inhibitor protein wherein 51 or 53 amino acid residues, respectively, at the carboxyl terminus of the mature protein are removed. Accordingly, a skilled artisan would appreciate that the fourth domain of each of the 30 kDa TNF inhibitor and the 40 kDa inhibitor is not necessary for TNF inhibition. In fact, various groups have confirmed this understanding. Domain-deletion derivatives of the 30 kDa and 40 kDa TNF inhibitors have been generated, and those derivatives without the fourth domain retain full TNF binding activity while those derivatives without the first, second or third domain, respectively, do not retain TNF binding activity; Corcoran et al., *Eur. J. Biochem.*, 223:831-840 (1994); Chih-Hsueh et al., *The Journal of Biological Chemistry*, 270(6):2874-2878 (1995); and Scallon et al., *Cytokine*, 7(8):759-770 (1995).

PCT WO US97/12244 describes functionally active truncated forms of sTNFR-I and sTNFR-II (referred to as "truncated sTNFR(s)). The truncated sTNFRs are modified forms of sTNFR-I and sTNFR-II which do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, which do not contain a portion of the first domain (amino acid residues $Asp^{1}$-$Cys^{19}$ of sTNFR-I and amino acid residues $Leu^{1}$-$Cys^{32}$ of sTNFR-II).

PEG-rmet-Hu-sTNF-R (PEGsTNF-R) as described herein is a recombinant form of a functionally active truncated form of sTNFR-I and sTNFR-II which has been PEGylated at the N-terminus with, e.g., a 30 kDa polyethylene glycol molecule. In our preliminary studies with PEGsTNF-R1 it was found that as the PEGsTNF-R1 is concentrated, the viscosity of the solution increases exponentially. Large scale methods traditionally used for concentrating proteins are known to be unsatisfactory when working with such viscous solutions, and the increased viscosity may prevent concentrating the protein to high concentrations without damaging the final product. Because there may be instances in a commercial setting where it will be necessary to have the protein at a higher concentration (e.g., >45 mg/ml) in order to deliver to required therapeutic dose, there is a need to develop formulations which obtain such concentrations and with acceptable low viscosities (e.g., <400 cP) to allow for the use of the various delivery devices necessary for delivery of the therapeutic dose. For example, in order to deliver the required therapeutic dose of a PEGsTNF-R1 formulation wherein the PEGsTNF-R1 concentration is >45 mg/ml, and using a commercially available autoinjector and pre-filled syringe as the delivery device, the formulation should have a viscosity of <400 cP. Above this viscosity, the strong possibility exists for the device or container to fail. The present invention provides for PEGsTNF-R1 formulations having such concentrations and low viscosities, thereby allowing for use of delivery devices which are more convenient and patient-friendly.

SUMMARY OF THE INVENTION

It is an object of the present invention to provide a new and improved formulation of PEGsTNF-R1, wherein said formulation has a concentration of at least 45 mg/ml without apparent damage to the protein, and with decreased viscosity (<400 cP) and improved stability.

Also provided are methods of preparing such formulations, said methods being capable of being scaled up to accommodate a commercial setting.

DETAILED DESCRIPTION OF THE INVENTION

Polypeptide is defined herein as natural, synthetic, and recombinant proteins or peptides having more than about 10 amino acids, and having a desired biological activity. Proteins contemplated for use herein would include but are not limited to interferon consensus (see, U.S. Pat. Nos. 5,372,808, 5,541, 293 4,897,471, and 4,695,623 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), stem cell factor (PCT Publication Nos. 91/05795, 92/17505 and 95/17206, hereby incorporated by reference including drawings), osteoprotegerin (PCT Publication No. 97/23614, hereby incorporated by reference including drawings), novel erythropoiesis stimulating protein (NESP) (PCT Publication No. 94/09257, hereby incorporated by reference including drawings), leptin (OB protein) (see PCT publication Nos. 96/40912, 96/05309, 97/00128, 97/01010 and 97/06816 hereby incorporated by reference including figures), megakaryocyte growth differentiation factor (see, PCT Publication No. 95/26746 hereby incorporated by reference including figures), tumor necrosis factor inhibitors, e.g., sTNF-R1 (see, PCT WO US97/12244 hereby incorporated by reference including figures), interleukin-1 receptor antagonist (IL-1ra), brain derived neurotrophic factor (BDNF), glial derived neurotrophic factor (GDNF), keratinocyte growth factor (KGF) and thrombopoietin. The term proteins, as used herein, includes peptides, polypeptides, consensus molecules, analogs, derivatives or combinations thereof.

In general, the sTNFRs contemplated for use in the present invention are those described in PCT WO US97/12244, and references cited therein. Specifically, the sTNFRs will be the truncated sTNFRs described therein. The truncated sTNFRs may advantageously be produced via recombinant techniques in bacterial, mammalian or insect cell systems and may be either a glycosylated or non-glycosylated forms of the protein. Alternatively, truncated sTNFRs may be chemically synthesized. Currently preferred production methods are described in PCT WO US97/12244.

Truncated sTNFRs each may typically be isolated and purified to be substantially free from the presence of other proteinaceous materials (i.e., non-truncated sTNFRs). Preferably, a truncated sTNFR is about 80% free of other proteins which may be present due to the production technique used in the manufacture of the truncated sTNFR. More preferably a truncated sTNFR is about 90% free of other proteins, particularly preferably about 95% free of other proteins, and most preferably about >98% free of other proteins. Currently preferred isolation and purification methods are described in PCT WO US97/12244. It will be appreciated, however, that the desired protein may be combined with other active ingredients, chemical compositions and/or suitable pharmaceutical formulation materials prior to administration.

In one aspect of the present invention, the truncated sTNFRs will be derivatized by attaching the truncated sTNFRs to a water soluble polymer. For example, the truncated sTNFRs will be conjugated to one or more polyethylene glycol molecules in order to improve pharmacokinetic performance by increasing the molecule's apparent molecular weight.

Water soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof.

As used herein, polyethylene glycol is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

The water soluble polymers each may be of any molecular weight and may be branched or unbranched. The water soluble polymers each typically have an average molecular weight of between about 2 kDa to about 100 kDa (the term "about" indicating that in preparations of a water soluble polymer, some molecules will weigh more, some less, than the stated molecular weight). The average molecular weight of each water soluble polymer preferably is between about 5 kDa and about 50 kDa, more preferably between about 12 kDa and about 40 kDa and most preferably between about 20 kDa and about 35 kDa.

Generally, the higher the molecular weight or the more branches, the higher the polymer:protein ratio. Other sizes may be used, depending on the desired therapeutic profile (e.g., the duration of sustained release; the effects, if any, on biological activity; the ease in handling; the degree or lack of antigenicity and other known effects of a water soluble polymer on a therapeutic protein).

The water soluble polymers each should be attached to the protein with consideration of effects on functional or antigenic domains of the protein. In general, chemical derivatization may be performed under any suitable condition used to react a protein with an activated polymer molecule. Activating groups which can be used to link the water soluble polymer to one or more proteins include the following: sulfone, maleimide, sulfhydryl, thiol, triflate, tresylate, azidirine, oxirane and 5-pyridyl.

The water soluble polymers each are generally attached to the protein at the α- or ε-amino groups of amino acids or a reactive thiol group, but it is also contemplated that a water soluble group could be attached to any reactive group of the protein which is sufficiently reactive to become attached to a water soluble group under suitable reaction conditions. Thus, a water soluble polymer may be covalently bound to a protein via a reactive group, such as a free amino or carboxyl group. The amino acid residues having a free amino group may include lysine residues and the N-terminal amino acid residue. Those having a free carboxyl group may include aspartic acid residues, glutamic acid residues and the C-terminal amino acid residue. Those having a reactive thiol group include cysteine residues.

Methods for preparing proteins conjugated with water soluble polymers will each generally comprise the steps of (a) reacting a protein with a water soluble polymer under conditions whereby the protein becomes attached to one or more water soluble polymers and (b) obtaining the reaction product. Reaction conditions for each conjugation may be selected from any of those known in the art or those subsequently developed, but should be selected to avoid or limit exposure to reaction conditions such as temperatures, solvents and pH levels that would inactivate the protein to be modified. In general, the optimal reaction conditions for the reactions will be determined case-by-case based on known parameters and the desired result. For example, the larger the ratio of water soluble polymer:protein conjugate, the greater the percentage of conjugated product. The optimum ratio (in terms of efficiency of reaction in that there is no excess unreacted protein or polymer) may be determined by factors such as the desired degree of derivatization (e.g., mono-, di-, tri-, etc.), the molecular weight of the polymer selected, whether the polymer is branched or unbranched and the reaction conditions used. The ratio of water soluble polymer (e.g., PEG) to protein will generally range from 1:1 to 100:1. One or more purified conjugates may be prepared from each mixture by standard purification techniques, including among others, dialysis, salting-out, ultrafiltration, ion-exchange chromatography, gel filtration chromatography and electrophoresis.

A variety of approaches have been used to attach the polyethylene glycol molecules to the protein (PEGylation). For example, Royer (U.S. Pat. No. 4,002,531) states that reductive alkylation was used for attachment of polyethylene glycol molecules to an enzyme. Davis et al. (U.S. Pat. No. 4,179,337) disclose PEG:protein conjugates involving, for example, enzymes and insulin. Shaw (U.S. Pat. No. 4,904,584) disclose the modification of the number of lysine residues in proteins for the attachment of polyethylene glycol molecules via reactive amine groups. Hakimi et al. (U.S. Pat. No. 5,834,594) disclose substantially non-immunogenic water soluble PEG:protein conjugates, involving for example, the proteins IL-2, interferon alpha, and IL-1ra. The methods of Hakimi et al. involve the utilization of unique linkers to connect the various free amino groups in the protein to PEG. Kinstler et al. (U.S. Pat. Nos. 5,824,784 and 5,985,265) teach methods allowing for selectively N-terminally chemically modified proteins and analogs thereof, including G-CSF and consensus interferon. Importantly, these modified proteins have advantages as relates to protein stability, as well as providing for processing advantages.

The preferred method of the present invention is the selective N-terminal chemical modification as described by Kinstler et al. (U.S. Pat. Nos. 5,824,784 and 5,985,265). As taught by Kinstler et al., one may selectively attach a water soluble polymer to the N-terminus of the protein by performing the reaction at a pH which allows one to take advantage of the pKa differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above and should have a single reactive aldehyde for coupling to the protein. Polyethylene glycol propionaldehyde, containing a single reactive aldehyde, may be used.

By such selective derivatization, attachment of a water soluble polymer (that contains a reactive group such as an aldehyde) to a protein is controlled: the conjugation with the polymer takes place predominantly at the N-terminus of the protein and no significant modification of other reactive groups, such as the lysine side chain amino groups, occurs. The preparation will typically be greater than 90% monopolymer/protein conjugate, and more typically greater than 95% monopolymer/protein conjugate, with the remainder of observable molecules being unreacted (i.e., protein lacking the polymer moiety).

A specific embodiment of the present invention is an unbranched monomethoxy-polyethylene glycol aldehyde molecule having an average molecular weight of either about 20 kDa or about 33 kDa (e.g., between 30 kDa and 35 kDa), or a tertiary-butyl polyethylene glycol aldehyde having an average molecular weight of about 33 kDa (e.g., between 30 kDa and 35 kDa) conjugated via reductive alkylation to a truncated sTNFR, wherein the truncated sTNFR has the amino acid sequence depicted in SEQ ID NO: 1.

The pegylation also may specifically be carried out via water soluble polymers having at least one reactive hydroxy group (e.g. polyethylene glycol) reacted with a reagent having a reactive carbonyl, nitrile or sulfone group to convert the hydroxyl group into a reactive Michael acceptor, thereby forming an "activated linker" useful in modifying various proteins to provide improved biologically-active conjugates. "Reactive carbonyl, nitrile or sulfone" means a carbonyl, nitrile or sulfone group to which a two carbon group is bonded having a reactive site for thiol-specific coupling on the second carbon from the carbonyl, nitrile or sulfone group (WO 92/16221). The activated linkers can be monofunctional, bifunctional, or multifunctional. Useful reagents having a reactive sulfone group that can be used in the methods include, without limitation, chlorosulfone, vinylsulfone and divinylsulfone.

PCT International Application No. US96/19459, the disclosure of which is hereby incorporated by reference, teaches methods of making sulfone-activated linkers by obtaining a compound having a reactive hydroxyl group and converting the hydroxyl group to a reactive Michael acceptor to form an activated linker, with the use of tetrahydrofuran (THF) as the solvent for the conversion. Also described is a process for purifying the activated linkers which utilizes hydrophobic interaction chromatography to separate the linkers based on size and end-group functionality.

Pharmaceutical compositions of the present invention will generally include a therapeutically effective amount of a chemically-modified derivative of truncated sTNFRs in admixture with a vehicle. The primary solvent in a vehicle may be either aqueous or non-aqueous in nature. In addition, the vehicle may contain other pharmaceutically acceptable excipients. Excipient is defined herein as a non-therapeutic agent added to a pharmaceutical composition to provide a desired effect, e.g. stabilization, isotonicity. Common attributes of desirable excipients are aqueous solubility, non-toxicity, non-reactivity, rapid clearance from the body, and the absence of immunogenicity. In addition, the excipients should be capable of stabilizing the native conformation of the protein so as to maintain the efficacy and safety of the drug during processing, storage and administration to the patient.

It is envisioned that the formulations of the present invention will additionally contain a buffering agent, e.g., alkali salts (sodium or potassium phosphate or their hydrogen or dihydrogen salts), sodium citrate/citric acid, sodium acetate/acetic acid, and any other pharmaceutically acceptable ph buffering agent known in the art, to maintain the pH of the solution within a desired range. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. The preferred pH of the preferred formulations will be in the range of 4.0 to 5.0, and pH-adjusting agents such as hydrochloric acid, citric acid, sodium hydroxide, or a salt thereof, may also be included in order to obtain the desired pH.

The formulations of the present invention may further include one or more tonicity modifiers to render the solution isotonic with a patient's blood for injection. Typical tonicity modifiers are well known in the art and include but are not limited to various salts, amino acids or polysaccharides. Non-limiting examples of suitable amino acids include glycine. Non-limiting examples of suitable polysaccharides include sucrose, mannitol and sorbitol. It is understood that more than one tonicity modifier may be used at once, for example, sorbitol and glycine can be used in combination to modify a formulation's tonicity.

It is also envisioned that other anti-oxidants may be included in the formulations of the present invention. Anti-oxidants contemplated for use in the preparation of the formulations include amino acids such as glycine and lysine, chelating agents such as EDTA and DTPA, and free-radical scavengers such as sorbitol and mannitol.

Other effective administration forms such as parenteral slow-release formulations, inhalant mists, orally-active formulations, or suppositories are also envisioned. As such, the formulations may also involve particulate preparations of polymeric compounds such as bulk erosion polymers (e.g., poly(lactic-co-glycolic acid) (PLGA) copolymers, PLGA polymer blends, block copolymers of PEG, and lactic and glycolic acid, poly(cyanoacrylates)); surface erosion polymers (e.g., poly(anhydrides) and poly(ortho esters)); hydrogel esters (e.g., pluronic polyols, poly(vinyl alcohol), poly (vinylpyrrolidone), maleic anhydride-alkyl vinyl ether copolymers, cellulose, hyaluronic acid derivatives, alginate, collagen, gelatin, albumin, and starches and dextrans) and composition systems thereof; or preparations of liposomes or microspheres. Such formulations may influence the physical state, stability, rate of in vivo release, and rate of in vivo clearance of the present proteins and derivatives. The optimal pharmaceutical formulation for a desired protein will be determined by one skilled in the art depending upon the route of administration and desired dosage. Exemplary pharmaceutical formulations are disclosed in *Remington's Pharmaceutical Sciences,* 18th Ed. (1990), Mack Publishing Co., Easton, Pa. 18042, pages 1435-1712, the disclosure of which is incorporated herein by reference.

Filtration is a pressure driven separation process that uses membranes to separate components in a liquid or suspension based on their size and charge differences. Membrane-based Tangential Flow Filtration (TFF) unit operations are commonly used for clarifying, concentrating, and purifying proteins. In TFF, the fluid is pumped tangentially along the surface of the membrane. An applied pressure serves to force a portion of the fluid through the membrane to the filtrate side. The retained components do not build up at the surface of the membrane, and instead they are swept along by the tangential flow. TFF can be further categorized base on the size of components being separated. A membrane pores size rating, typically given as a micron value, indicates that particles larger than the rating will be retained by the membrane. A nominal molecular weight limits (NMWL) is an indication that most dissolved macromolecules with molecular weights higher than the NMWL and some with molecular weights lower than the NMWL will be retained by the membrane. A components shape, its ability to deform, and its interaction with other components in the solution all affect its retention.

Ultrafiltration (UF) is one of the most widely used forms of TFF and is used to separate proteins from buffer components for buffer exchange, desalting, and concentration. Depending on the protein to be retained, membranes NMWLs in the range of 1 kD to 1000 kD are used. The typical sequences of steps in an ultrafiltration process include cleaning the membranes and the system, testing the integrity and permeability, equilibrating with process buffer, concentrating the sample containing the product, removing product from system, cleaning the membranes and the system, testing integrity and permeability, and storing.

The most important factors in design of UF processes include product yield, product quality, process time, and process economics. Yield losses in a UF process can be generally be attributed to sieving, solubility limitations, adsorption to the membrane, and unrecoverable volumetric losses. While several key process parameters such as transmembrane pressure, crossflow rate, and membrane area need to be optimized, protein concentration is one of the limiting factors in developing a TFF step. Since there is the potential for highly concentrated areas to exist within the TFF unit as the result of the polarization, high protein concentration can exceed a solubility limitation and increase fouling behavior at membrane surface. The significant increased viscosity (e.g., >500 cP) associated with the concentration of certain pegylated protein causes process difficulties in term of maintaining crossflow rate and minimizing heat introduction. The present invention provides an improved ultrafiltration process to concentrate PEGsTNF-R1 to greater than 45 mg/ml by utilizing a improved formulation and temperature effect.

The process of lyophilization is very well documented in literature. Lyophilization is the process by which the moisture content of the product is reduced by freezing and subsequent sublimation under vacuum. The lyophilization process primarily consists of three stages. The first stage involves freezing the product and creating a frozen matrix suitable for drying. This step impacts the drying characteristics in the next two stages. The second stage is primary drying. Primary drying involves the removal of the ice by sublimation by reducing the pressure (to typically around 50-500 μm Hg) of the product's environment while maintaining the product temperature at a low, desirable level. The third stage in the process is called secondary drying where the bound water is removed until the residual moisture content reaches below the target level.

Lyophilization improves product stability by (a) maintaining the protein in an amorphous phase with its stabilizers, (b) immobilizing the protein in a glassy phase below the glass transition temperature (Tg') of the formulation, and (c) reducing the residual moisture content to a low, desirable value. Maintaining the protein in an amorphous phase with its stabilizers helps in protecting the protein. Keeping the dried protein below its glass transition temperature minimizes protein immobility on all practical time-scales and therefore prevents degradation. Reducing the amount of residual water minimizes all water-catalyzed degradations.

A freeze dryer consists of a chamber with shelves on to which the filled vials are loaded for lyophilization, a condenser for capturing the product's sublimed water vapor as ice, a refrigeration system that facilitates temperature control, and a vacuum pump which can reduce the chamber pressure to sub-atmospheric values. The chamber pressure is maintained at its set-point by introducing, in a controlled manner, an inert, dry bleed gas (such as nitrogen) at the front of the chamber. In most cases, the chamber is separated from the condenser via a main valve. The product is loaded onto the stainless steel shelves, whose temperature is controlled via a heat-transfer fluid (silicone oil) circulating through the shelves. Temperature of the heat-transfer fluid is controlled via the refrigeration system.

The freezing stage is initiated by cooling the shelves to the desired freezing temperature and holding the temperature constant for equilibration. The cooled shelves help freeze the product to the desired temperature. Following freezing, the chamber pressure (measured by a capacitance manometer) is reduced to below the saturated vapor pressure of ice at the frozen temperature. This initiates primary drying. Since ambient pressure is below the saturated vapor pressure at that temperature, part of the frozen product instantaneously sublimes (the difference between the vapor pressure of ice and the chamber pressure provides the driving force for sublimation). Sublimation leads to pressure equilibration. However, since the chamber pressure is constantly maintained below the saturated vapor pressure of ice (at that temperature), sublimation continues. The sublimed vapors are trapped at the condenser as ice. Typically, the condenser coil or plates remain at about −50° C. to −70° C. during the drying process. When all the bulk water is removed via sublimation, primary drying is complete. At this point, there is still some bound water remaining in the product which can be removed by desorption at higher temperatures experienced during secondary drying. So, typically the shelf-temperature is raised at this stage and held, until the desired residual moisture is achieved. At that point, secondary drying is also complete, and the vials are stoppered in the chamber. The chamber is aerated prior to the unloading of the vials. Note that the above description is generic, and some equipment design variations are available.

The objective of a lyophilization process is to achieve a freeze-dried protein cake with acceptable appearance, biological potency, ease of reconstitution, and long-term storage stability. A prudently designed lyophilization cycle is one that is robust, consumes less time and energy, and maintains product quality. Both formulation-related and cycle-related factors contribute to achieving this goal.

For freeze-dried products, the formulation and the lyophilization process are intricately interrelated. As mentioned earlier, to maintain product stability, the product temperature needs to be below its glass transition temperature (Tg') both during drying and storage. Therefore, a formulation with a higher Tg' allows drying at a higher temperature compared with a lower-Tg'-formulation and subsequently expedites the freeze-drying time. Since Tg' of the formulation is approximately the mass-average of Tg' values of all the amorphous components in the formulation, the Tg' of the formulation can be raised by increasing the weight fraction of high-Tg' components of the formulation and/or by decreasing the weight fraction of low-Tg' components. Of course, it is necessary that the chosen excipients regardless of their Tg' values, protect the protein from possible degradations.

The addition of a lyophilization excipient in the processes described herein may be necessary. One or more excipients may be added. The lyophilization excipient(s) contemplated for use in the present processes include sucrose, lactose, mannitol, dextran, sucrose, heparin, glycine, glucose, glutamic acid, gelatin, sorbitol, histidine, dextrose, trehalose, methocel, hydroxy ethyl cellulose, hydroxy ethyl starch, poly (ethylene glycol), poly(vinyl pyrolidone) and polyvinyl alcohol, or various combinations thereof, as well as other buffers, protein stabilizers, cryoprotectants, and cyropreservatives commonly used by those skilled in the art. The present invention provides an improved lyophilization and reconstitution method for concentrating PEGsTNF-R1 to greater than 45 mg/ml.

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like consensus interferon (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, 5,621,080, 5,756,349, and 5,955,422, hereby incorporated by reference including drawings), granulocyte-colony stimulating factors (see, U.S. Pat. Nos. 4,999,291, 5,581,476, 5,582,823, 4,810, 643 and PCT Publication No. 94/17185, hereby incorporated by reference including drawings), megakaryocyte growth differentiation factor (see, PCT Publication No. 95/26746), stem cell factor (PCT Publication Nos. 91/05795, 92/17505 and 95/17206, hereby incorporated by reference including drawings), OB protein (see PCT publication Nos. 96/40912, 96/05309, 97/00128, 97/01010 and 97/06816 hereby incorporated by reference including figures), and novel erythropoiesis stimulating protein (PCT Publication No. 94/09257, hereby incorporated by reference including drawings). In addition, the present compositions may also be used for manufacture of one or more medicaments for treatment or amelioration of the conditions the biologically active agent is intended to treat.

As relates specifically to PEGsTNFR1, the present invention provides for methods for the treatment of certain diseases and medical conditions (many of which can be characterized as inflammatory diseases) that are mediated by TNF. A disease or medical condition is considered to be a "TNF-mediated disease" if the spontaneous or experimental disease is associated with elevated levels of TNF in bodily fluids or in tissues adjacent to the focus of the disease or indication within the body. TNF-mediated diseases may also be recognized by the following two conditions: (1) pathological findings associated with a disease can be mimicked experimentally in animals by the administration of TNF and (2) the pathology induced in experimental animal models of the disease can be inhibited or abolished by treatment with agents which inhibit the action of TNF. Many TNF-mediated diseases satisfy two of these three conditions, and others will satisfy all three conditions. A non-exclusive list of TNF-mediated diseases, as well as the related sequela and symptoms associated therewith, is adult respiratory distress syndrome; cachexia/anorexia; cancer (e.g., leukemias); chronic fatigue syndrome; congestive heart failure; graft versus host rejection; hyperalgesia; inflammatory bowel disease; neuroinflammatory diseases; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjögren's syndrome, rheumatic fever, polychondritis and polymyalgia rheumatica and giant cell arteritis); septic shock; side effects from radiation therapy; systemic lupus erythematous; temporal mandibular joint disease; thyroiditis and tissue transplantation. Specifically, TNF-mediated diseases (e.g., diseases mediated by TNF-α and/or TNF-β) may be treated by administering to a patient therapeutically effective amounts of truncated sTNFRs or derivatives thereof.

The PEGsTNF-R1 products each may be administered to a patient in therapeutically effective amounts for the treatment of TNF-mediated diseases, as defined above, including such as rheumatic diseases (e.g., lyme disease, juvenile (rheumatoid) arthritis, osteoarthritis, psoriatic arthritis, rheumatoid arthritis and staphylococcal-induced ("septic") arthritis). The term "patient" is intended to encompass animals (e.g., cats, dogs and horses) as well as humans.

A PEGsTNF-R1 product may be administered via topical, enteral or parenteral administration including, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, intraventricular and intrasternal injection and infusion. A truncated sTNFR product may also be administered via oral administration or be administered through mucus membranes, that is, intranasally, sublingually, buccally or rectally for systemic delivery.

It is preferred that PEGsTNF-R1 products be administered via intra-articular, subcutaneous, intramuscular or intravenous injection. Additionally, PEGsTNFR1 product may be administered by a continuous infusion (e.g., constant or intermittent implanted or external infusion flow-modulating devices) so as to continuously provide the desired level of PEGsTNFR1 product in the blood for the duration of the administration. This is preferably accomplished by means of continuous infusion via, e.g., mini-pump such as osmotic mini-pump. In these ways, one can be assured that the amount of drug is maintained at the desired level and one can take blood samples and monitor the amount of drug in the bloodstream. Various pumps are commercially available, from suppliers such as MiniMed Inc, Sylmar, Calif. (e.g., MT507) and Alza Corp., Palo Alto, Calif. (e.g., Alzet osmotic pump, model 2MLI).

PEGsTNF-R1 may be administered using an autoinjector type device. These devices typically use a pre-filled syringe or pre-filled cartridge with the device. The device is held against the injection site, a needle inserts through the skin and injects the drug in approximately 5-30 seconds depending on the device and syringe configuration. The use of commercially available devices and syringes requires viscosities of <400 cp for an injection to occur in a reasonable time, i.e. <30 seconds and more preferably <15 seconds. Commercial suppliers are Scandinavian Health Ltd. Far Eastern World Center, 11th Floor-8, #77, Hsin Tai Wu Rood, Sec. 1, Hsih Chih, Taipei, Taiwan, R.O.C., and Owen Mumford Ltd. Brook Hill, Woodstock, Oxford OX20 1TU, England.

It is also contemplated that other modes of continuous or near-continuous dosing may be practiced. For example, chemical derivatization may result in sustained release forms of the protein which have the effect of continuous presence in the blood stream, in predictable amounts based on a determined dosage regimen.

Modes of using PEGsTNF-R1 products for the treatment of TNF-mediated diseases, including inflammatory conditions of a joint (e.g., osteoarthritis, psoriatic arthritis and rheumatoid arthritis), are set forth in European Patent Application 567566, the teachings of which are hereby incorporated by reference. By way of example but not limitation, in one specific embodiment PEGsTNFR1 products may be administered intra-articularly for the treatment of rheumatoid arthritis and osteoarthritis. By way of example but not limitation in another specific embodiment, PEGsTNF-R1 products may be administered subcutaneously or intramuscularly for the treatment of rheumatoid arthritis, inflammatory bowel disease, cachexia/anorexia or multiple sclerosis. By way of example but not limitation, in a still further specific embodiment PEGsTNF-R1 products may be administered intravenously for the treatment of brain injury as a result of trauma, epilepsy, hemorrhage or stroke; or administered intraventricularly for the treatment of brain injury as a result of trauma. A preferred mode for the treatment of arthritis includes: (1) a single intra-articular injection of a PEGsTNF-R1 product given periodically as needed to prevent or remedy the flare-up of arthritis and (2) periodic subcutaneous injections of a PEGsTNFR1 product. The initiation of treatment for septic shock should begin as soon as possible after septicemia or the chance of septicemia is diagnosed. For example, treatment may be begun immediately following surgery or an accident or any other event that may carry the risk of initiating septic shock. Preferred modes for the treatment of adult respiratory distress syndrome include: (1) single or multiple intratracheal administrations of a PEGsTNF-R1 product and (2) bolus or continuous intravenous infusion of a PEGsTNF-R1 product. Regardless of the manner of administration, the treatment of a TNF-mediated disease requires a dose or total dose regimen of a PEGsTNF-R1 effective to reduce or alleviate symptoms of the disease. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information ad assays disclosed herein. The dosage can also be determined through the use of known assays for determining dosages used in conjunction with appropriate dose-response data. The specific dose is calculated according to the approximate body weight or body surface area of the patient.

The frequency of dosing depends on the pharmacokinetic parameters of the PEGsTNF-R1 in the formulation used. The PEGsTNF-R1 may be administered once, or in cases of severe and prolonged disorders, administered daily in less frequent doses or administered with an initial bolus dose followed by a continuous dose or sustained delivery. When administered parenterally, parenteral unit doses, for example, may each be up to 10 mg, generally up to 15 mg and more generally up to 20 mg. When administered into an articular cavity, the pharmaceutical composition is preferably administered as a single injection from, for example, a 3 to 10 ml syringe containing a dose, for example, of between about 5 mg/ml to 10 mg/ml truncated sTNFR dissolved in isotonic phosphate buffered saline. The preparation may be administered into an articular cavity at a frequency, for example, of once every 7 to 10 days. In such a manner, the administration is continuously conducted, for example, 4 to 5 times while varying the dose if necessary.

In some cases, PEGsTNF-R1 products may be administered as an adjunct to other therapy and also with other pharmaceutical formulations suitable for the indication being treated. A PEGsTNF-R1 product and any of one or more traditional or new anti-inflammatory drugs may be administered separately or in combination.

Present treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis) includes first line drugs for control of pain and inflammation classified as non-steroidal, anti-inflammatory drugs (NSAIDs). Secondary treatments include corticosteroids, slow acting anti-rheumatic drugs (SAARDs) or disease modifying (DM) drugs. Additional TNF-mediated diseases contemplated are those described in PCT WO US97/12244.

Preferred PEGsTNF-R1 formulations contemplated for use in the present invention will contain one or more buffering agents such as, but not limited to acetate, histidine or phosphate; a tonicity modifier such as, but not limited to sucrose, sorbitol, mannitol, or glycine; an antioxidant such as, but not limited to methionine, EDTA, or ascorbate; an antimicrobial agent such as, but not limited to benzyl alcohol or phenol; a surfactant such as, but not limited to polysorbate 20 or polysorbate 80.

It is contemplated that when sorbitol is the tonicity modifier, it is between zero and 5.48%, more preferably 1% to 5.48%, more preferably 1.5% to 5.48%, more preferably 2% to 5.48%, and even more preferably 2.56% to 5.48%. It is contemplated that when glycine is the tonicity modifier, it is between zero and 2.19%, more preferably 1% to 2.19%, more preferably 1.25% to 2.19%, and even more preferably 1.5% to 2.19%. In one particular embodiment, the formulation comprises acetate buffer at between pH 4-5 and 2.56% Sorbitol. It is understood that the above percentages are based on weight/volume.

The following examples are offered to more fully illustrate the invention, but are not to be construed as limiting the scope thereof. Additional methods for reducing the solution viscosity of a PEGsTNFR1 formulation may include site-directed mutagenesis of specific amino acids or removal of amino acids sequences contained within the coding region of the sTNFR1 amino acid sequence.

EXAMPLE 1

This example describes experiments wherein PEGsTNF-RI at 45 cP and 336 cP was loaded into 1 ml syringes and injected with commercially available autoinjectors. The results of these studies are shown in the following table (Table 1). The standard autoinjector was modified to deliver the 336 cP solution.

TABLE 1

| Viscosity (cP) | Needle Size | Injection time (sec) |
|---|---|---|
| 45 | 26 | 10.5 |
| 45 | 27 | 42 |
| 336 | 23 | 9 |
| 336 | 25 | 78 |

The data demonstrate that while the autoinjector can deliver the low viscosity solution in less than 15 sec with the 26G syringe, a significantly larger needle was necessary to make an equivalent injection with the higher viscosity material. Smaller needles (26 or 27 G) are preferred over the larger needles (23 G) to reduce injection pain. This shows the importance of developing formulations of PEGsTNF-R1 having sufficiently high concentrations and with sufficiently low viscosities.

EXAMPLE 2

This example describes experiments wherein various concentrated samples of PEGsTNF-R1 were prepared and then viscosity measurements taken on concentrated samples.

The samples for this experiment were prepared by room temperature diafiltration at the indicated pH in 10 mM sodium acetate. The membranes used for the diafiltration were in the form of cassettes, and the membrane types were regenerated cellulose with nominal molecular weight cut-off value of 5 kD and 10 kD. The starting material enters through the feed port and buffer-exchanged product exits through the retentate port. Filtrate was removed from filtrate ports. Transmembrane pressure, crossflow rate, and filtrate flowrate were monitored and controlled during the process. After concentration of the protein, 140 mM sodium chloride (NaCl), 5.48% sorbitol, or 2.19% added and viscosity measurements taken.

Viscosity was measured using a Brookfield viscometer (Brookfield Instruments, USA). The system was temperature stated at 16° C. using a circulating water bath. Viscosity measurements were recorded after equilibration of the system. The results of this analysis are depicted in Table 2.

TABLE 2

| Sample # | pH of sample | Final protein concentration | Excipients | Viscosity (cP) |
|---|---|---|---|---|
| 1 | 5.0 | 59 mg/ml | none | 532 |
| 2 | 4.5 | 55 mg/ml | NaCl (0.9%) | 550 |
| 3 | 4.5 | 55 mg/ml | Sorbitol (5.48%) | 276 |
| 4 | 4.5 | 55 mg/ml | Glycine (2.19%) | 255 |

TABLE 2-continued

| Sample # | pH of sample | Final protein concentration | Excipients | Viscosity (cP) |
|---|---|---|---|---|
| 5 | 4.5 | 55 mg/ml | NaCl (0.30%) Glycine (0.723%) Sorbitol (1.81%) | 355 |
| 6 | 4.5 | 55 mg/ml | Glycine (1.10%) Sorbitol (2.74%) | 255 |
| 7 | 5.0 | 55 mg/ml | NaCl (0.9%) | 719 |
| 8 | 5.0 | 55 mg/ml | Sorbitol (5.48%) | 335 |
| 9 | 5.0 | 55 mg/ml | Glycine (2.19%) | 327 |
| 10 | 5.0 | 55 mg/ml | NaCl (0.30%) Glycine (0.723%) Sorbitol (1.81%) | 544 |
| 11 | 5.0 | 55 mg/ml | Glycine (1.10%) Sorbitol (2.74%) | 326 |
| 12 | 4.5 | 45 mg/ml | NaCl (0.9%) | 245 |
| 13 | 4.5 | 45 mg/ml | Sorbitol (5.48%) | 134 |
| 14 | 4.5 | 45 mg/ml | Glycine (2.19%) | 125 |
| 15 | 4.5 | 45 mg/ml | NaCl (0.30%) Glycine (0.723%) Sorbitol (1.81%) | 167 |
| 16 | 4.5 | 45 mg/ml | Glycine (1.10%) Sorbitol (2.74%) | 126 |
| 17 | 5.0 | 45 mg/ml | NaCl (0.9%) | 309 |
| 18 | 5.0 | 45 mg/ml | Sorbitol (5.48%) | 157 |
| 19 | 5.0 | 45 mg/ml | Glycine (2.19%) | 164 |
| 20 | 5.0 | 45 mg/ml | NaCl (0.30%) Glycine (0.723%) Sorbitol (1.81%) | 220 |
| 21 | 5.0 | 45 mg/ml | Glycine (1.10%) Sorbitol (2.74%) | 154 |

This example demonstrates that pH, protein concentration and additional excipients all affect the final viscosity, and that formulations having concentrations of up to 55 mg/ml and viscosities<400 cP can be obtained using sorbitol and/or glycine as a formulation excipient.

EXAMPLE 3

This example describes experiments wherein samples of PEGsTNF-R1 were lyophilized using varying pH's, protein concentrations, and lyophilization methods. The lypohilized samples were then reconstituted to concentrations>50 mg/ml and viscosity measurements taken.

PEGsTNF-R1 at 25 mg/ml for lyophilization was prepared as follows: PEGsTNF-R1 was buffer exchanged into water, concentrated using an Amicon stirred cell device, and diluted with 10× concentrated buffer to 25 mg/ml in 10 mM histidine, pH 4.0 or 5.5, 1% (w/v) sucrose, 2% (w/v) glycine and 0.01% polysorbate 20.

PEGsTNF-R1 at 60 mg/ml for lyophilization was prepared as follows: PEGsTNFR1 was buffer exchanged into water, concentrated using an Amicon stirred cell device, and diluted with 10× concentrated buffer to 25 mg/ml in 10 mM histidine, pH 4.0 or 5.5, 1.0% (w/v) sucrose, 2% (w/v) glycine and 0.01% polysorbate 20.

Samples were then lyophilized using the low temperature method or high temperature method as described in the Materials and Methods section below. After lyophilization, the samples were reconstituted with water to the desired protein concentration and with the following excipient concentrations: 5 mM histidine, pH 4.0 or 5.5, 0.5% (w/v) sucrose, 1% (w/v) glycine and 0.005% polysorbate 20. Viscosity was measured using a Haake falling ball microviscometer (Haake Instruments, Germany). The system was temperature stated at 26° C. using a circulating water bath. Viscosity measurements were recorded after equilibration of the system. The results of this analysis are depicted in Table 3.

TABLE 3

| Sample # | Lyophilization method | Solution for reconstitution | Final protein concentration after reconstitution | Viscosity (cP) |
|---|---|---|---|---|
| 1 | Lyophilized at 25 mg/ml and pH 4.0 | Low Temperature method | Sterile water | 57 mg/ml | 230 |
| 2 | Lyophilized at 25 mg/ml and pH 5.5 | Low Temperature method | Sterile water | 57 mg/ml | 515 |
| 3 | Lyophilized at 25 mg/ml and pH 4 | Low Temperature method | Sterile water | 72.2 mg/ml | 410* |
| 4 | Lyophilized at 25 mg/ml and pH 4 | Low Temperature method | 10% sucrose | 72.9 mg/ml | 570* |
| 5 | Lyophilized at 60 mg/ml and pH 4 | Low Temperature method | Sterile water | 50 mg/ml | 246 |
| 6 | Lyophilized at 60 mg/ml and pH 4 | High Temperature method | Sterile water | 60 mg/ml | 266 |

*Due to the high viscosity, samples were measured at 37° C.

This example again demonstrates that pH, protein concentration and additional excipients all affect the final viscosity, and that formulations having concentrations of at least 57 mg/ml and viscosities<400 cP can be obtained using various ultrafiltration/lyophilization techniques.

EXAMPLE 4

This example describes experiments wherein samples of PEGsTNFR1, at various concentrations, and containing various excipients, were tested for stability.

Samples for stability studies of PEGsTNFR1 at concentrations of 15 mg/ml were prepared by buffer exchanging the protein into deionized water using the tangential flow system described above. Excipients (e.g., histidine, acetate) were then added from stock solutions to their final concentrations and pH. The samples were then sterile filtered and 1 ml aliquots filled in 3 cc glass vials and incubated at the indicated temperature.

Samples for stability studies of PEGsTNFR1 at concentrations>45 mg/ml were buffer exchanged into 10 mM acetate. The pH after concentrating was 4.9. Excipients were added from stock solutions to the indicated concentrations. The samples were then sterile filtered and 1 ml aliquots filled in 3 cc glass vials and incubated at the indicated temperature.

Stability of PEGsTNFR1 was determined by high performance size exclusion chromatography. A TosoHaas TSKGSW300xL (7.8×300 mm) size exclusion column was equilibrated in buffer containing 10 mM sodium acetate pH 5.0, 0.5M sodium chloride, 10% ethanol (v/v). Protein was eluted using a flow rate of 0.5 ml/min. The results of this analysis are depicted in Table 4.

TABLE 4

| Buffer/ Excipients | Tonicity Modifier | pH | Protein (mg/ml) | Incubation Temp (° C.) | % Main Peak by SEC at 12 weeks |
|---|---|---|---|---|---|
| 10 mM Acetate | 140 mM NaCl | 4 | 15 | 4 | 92.9 |
| 10 mM Acetate | 140 mM NaCl | 5.5 | 15 | 4 | 93.4 |
| 10 mM Histidine | 140 mM NaCl | 5.5 | 15 | 4 | 93.3 |

TABLE 4-continued

| Buffer/ Excipients | Tonicity Modifier | pH | Protein (mg/ml) | Incubation Temp (° C.) | % Main Peak by SEC at 12 weeks |
|---|---|---|---|---|---|
| 10 mM Acetate | 140 mM NaCl | 4 | 15 | 37 | 67.2 |
| 10 mM Acetate | 140 mM NaCl | 5.5 | 15 | 37 | 87.3 |
| 10 mM Histidine | 140 mM NaCl | 5.5 | 15 | 37 | 82.0 |
| 10 mM Acetate | NaCl (140 mM) | 4.9 | 52 | 4 | 97.4 |
| 10 mM Acetate | Sorbitol (5.48%) | 4.9 | 45 | 4 | 97.0 |
| 10 mM Acetate | Glycine (2.19%) | 4.9 | 46 | 4 | 96.9 |
| 10 mM Acetate | NaCl (140 mM) | 4.9 | 52 | 37 | 73.1 |
| 10 mM Acetate | Sorbitol (5.48%) | 4.9 | 45 | 37 | 86.1 |
| 10 mM Acetate | Glycine (2.19%) | 4.9 | 46 | 37 | 88.4 |

The data demonstrate that pH, temperature, protein concentration and choice of excipients are all factors which affect the stability and that stable formulations having concentrations of >45 mg/ml can be prepared.

Materials and Methods

All chemicals were ACS grade or better.

The sTNFRs used in the present invention were prepared according to the above incorporated-by-reference PCT WO US97/12244.

The PEGsTNFR1 formulations used in the present invention were prepared using the selective N-terminal chemical modification as described by Kinstler et al. (U.S. Pat. Nos. 5,824,784 and 5,985,265).

The low temperature lyophilization of the PEGsTNF-R1 was carried out as follows: Vials were loaded onto a shelf equilibrated at 4° C. The shelf temperature was decreased to −50° C. at a cooling rate of 36° C./hr. After holding at −50° C. for two hours, the shelf temperature was increased to −15° C. at a heating rate of 35° C./hr and held there for two hours and 30 minutes. The samples were then brought back to −50° C. at a cooling rate of −23° C./hr. The primary drying was started by evacuating the chamber to 80 mTorr and held at −50° C. for an additional 30 minutes. The shelf temperature was brought to −25° C. at a heating rate of 12.5° C./hr, then kept at −25° C. for seventeen hours. The secondary drying was initiated by bringing the shelf temperature to 30° C. by heating at a rate of 5.5° C./hr. After 12 hours at 30° C., the secondary drying was complete.

The high temperature lyophilization of the PEGsTNF-R1 was carried out as follows: Vials were loaded onto a shelf equilibrated at 4° C. The shelf temperature was decreased to −40° C. at a cooling rate of 15° C./hr. After holding at −40° C. for two hours, the shelf temperature was increased to −15° C. at a heating rate of 10° C./hr and held there for two hours. The primary drying was started by evacuating the chamber to 80 mmHg. The shelf temperature was kept at −15° C. for one hour and then increased to 10° C. at a heating rate of 10° C./hr. The primary drying was continued for 30 hours at 10° C. The secondary drying was continued by increasing the shelf temperature to 30° C. at a heating rate of 10° C./hr. After 14 hours at 30° C., the secondary drying was complete.

The present invention has been described in terms of particular embodiments found or proposed to comprise preferred modes for the practice of the invention. It will be appreciated by those of ordinary skill in the art that, in light of the present disclosure, numerous modifications and changes can be made in the particular embodiments exemplified without departing from the intended scope of the invention.

What is claimed is:

1. A stable pharmaceutical formulation comprising at least 45 mg/ml PEGsTNF-R1, at least one tonicity modifier that is not NaCl, a surfactant and a buffer, wherein said pharmaceutical formulation is between pH 4.0 and 5.5 and wherein the viscosity is less than 400 cP.

2. The pharmaceutical formulation of claim 1 wherein the tonicity modifier is sorbitol and/or glycine.

3. The pharmaceutical formulation of claim 2 wherein the sorbitol is from zero to 5.48% (w/v).

4. The pharmaceutical formulation of claim 3 wherein the sorbitol is from 2.56% to 5.48% (w/v).

5. The pharmaceutical formulation of claim 3 wherein the sorbitol is 5.48% (w/v).

6. The pharmaceutical formulation of claim 2 wherein the glycine is from zero to 2.19% (w/v).

7. The pharmaceutical formulation of claim 6 wherein the glycine is from 1% to 2.19% (w/v).

8. The pharmaceutical formulation of claim 6 wherein the glycine is 2.19% (w/v).

9. The pharmaceutical formulation of claim 2 wherein the glycine is 1.10% (w/v) and the sorbitol is 2.74% (w/v).

10. The pharmaceutical formulation of claim 1 wherein the buffer is acetate.

11. The pharmaceutical formulation of claim 10 wherein the pH is 5.0.

12. The pharmaceutical formulation of claim 1 wherein the viscosity is less than 200 cP.

13. The pharmaceutical formulation of claim 1 wherein the PEGsTNF-R1 is 55 mg/ml.

14. A pre-filled syringe containing the pharmaceutical formulation of any one of claims 1-13.

15. An article of manufacture comprising a container holding a stable pharmaceutical formulation comprising at least 45 mg/ml PEGsTNF-R1 at least one tonicity modifier that is not NaCl, and a buffer, wherein said pharmaceutical formulation is between pH 4.0 and 5.5 and wherein the viscosity is less than 400 cP.

16. A method of making a stable pharmaceutical formulation comprising:
 a) admixing at least 45 mg/ml PEGsTNF-R1, at least one tonicity modifier that is not NaCl, and a buffer, and
 b) adjusting the pH to between pH 4.0 and 5.5, wherein said pharmaceutical formulation has a viscosity less than 400 cP.

* * * * *

UNITED STATES PATENT AND TRADEMARK OFFICE
CERTIFICATE OF CORRECTION

| | | |
|---|---|---|
| PATENT NO. | : 7,700,722 B2 | Page 1 of 1 |
| APPLICATION NO. | : 10/461839 | |
| DATED | : April 20, 2010 | |
| INVENTOR(S) | : Kerwin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1375 days.

Signed and Sealed this
Eleventh Day of January, 2011

David J. Kappos
*Director of the United States Patent and Trademark Office*